United States Patent [19]
Wada et al.

[11] Patent Number: 5,095,751
[45] Date of Patent: Mar. 17, 1992

[54] ACCELERATION SENSOR

[75] Inventors: Shunichi Wada; Masayuki Yano, both of Hyogo, Japan

[73] Assignee: Mitsubishi Denki K.K., Tokyo, Japan

[21] Appl. No.: 455,015

[22] Filed: Dec. 22, 1989

[30] Foreign Application Priority Data

Dec. 23, 1988 [JP] Japan .................. 63-167296
Dec. 23, 1988 [JP] Japan .................. 63-327129

[51] Int. Cl.⁵ ........................................... G01P 15/09
[52] U.S. Cl. ..................................... 73/517 R; 73/654
[58] Field of Search ............... 73/654, 517 R, 431; 310/319, 329

[56] References Cited

U.S. PATENT DOCUMENTS

| | | | |
|---|---|---|---|
| 4,085,349 | 4/1978 | Farstad | 310/319 |
| 4,417,476 | 11/1983 | Knowlton | 73/660 |
| 4,441,370 | 4/1984 | Sakurada | 73/651 |
| 4,620,442 | 11/1986 | MacGugan et al. | 73/517 R |
| 4,801,838 | 1/1989 | Beauducel | 310/319 |
| 4,816,713 | 3/1989 | Change | 310/329 |

FOREIGN PATENT DOCUMENTS 1258176 12/1971 United Kingdom .
1277768 6/1972 United Kingdom .

Primary Examiner—John E. Chapman
Attorney, Agent, or Firm—Sughrue, Mion, Zinn, Macpeak & Seas

[57] ABSTRACT

An acceleration sensor is disclosed which includes a weight, piezoelectric element(s), a charge amplifier, an insulation plate and a conductive casing. The insulation plate fixedly mounts the weight and piezoelectric element(s) and is fixed to the conductive casing which is maintained at the earth potential. Input terminals of the charge amplifier are connected to the output electrodes of the element(s) and a grounding circuit of the amplifier is connected to the conductive casing so that the input terminals of the amplifier are floated from the earth potential.

8 Claims, 4 Drawing Sheets

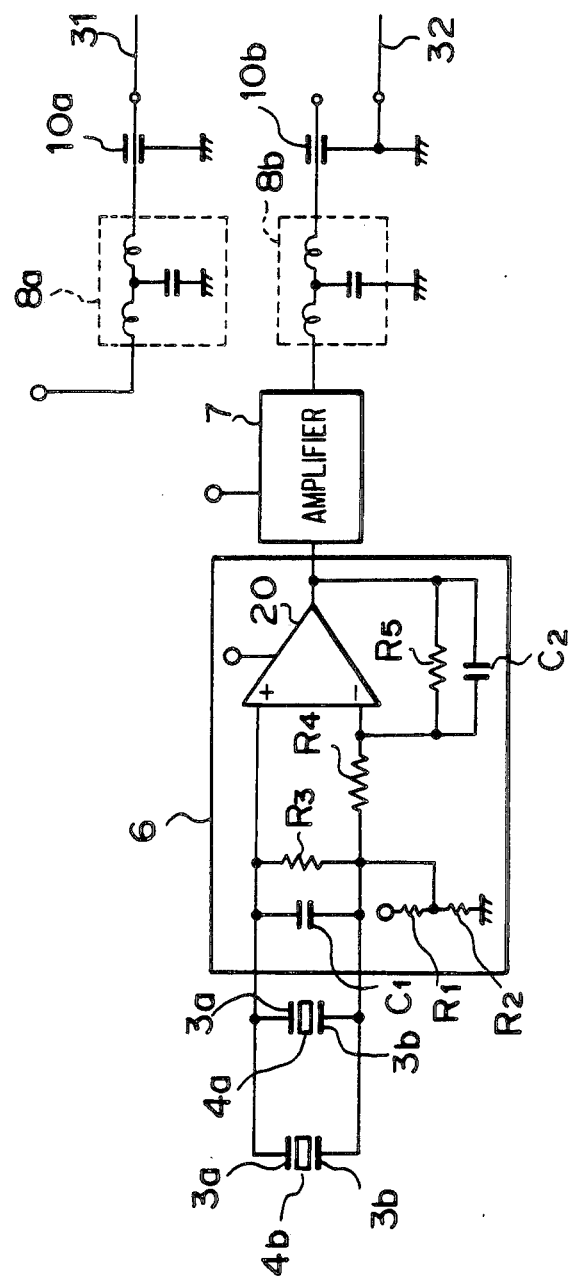

ACCELERATION SENSOR

BACKGROUND OF THE INVENTION

1. Field of the Invention

The present invention relates to an acceleration sensor which employs piezoelectric element(s) adapted to detect vibration in an automobile or the like.

2. Prior Art

A piezoelectric type sensor has been used for detecting vibration in an automobile. This piezoelectric sensor is described for example in "Force and Acceleration Sensor (1)" p. 81-85, by Keras, Series No. 5, Ceramic Sensor, 1973, No. 32 Ele-Cera Publishing Co.

An acceleration sensor employing such a piezoelectric sensor as described above, a weight, and a charged amplifier is applied for example to an electric control suspension means adapted to control vibration in an automobile in order to improve the driving and riding feel.

In the case that the piezoelectric sensor is applied to the electronic control suspension means, since the piezoelectric sensor has a high impedance and is capacitive, coping with external noise is a problem.

Accordingly, there have been proposed such measures as to incorporate an impedance conversion circuit, and to ground one of the electrodes of a piezoelectric sensor to a casing so that the casing provides a shielding effect.

However, in this instance, in such an application as an automobile in which a single battery power source is available for activation and the body of the automobile is grounded, if one of the electrodes of a piezoelectric sensor is grounded to the casing, a signal for detecting acceleration is variable mainly relative to the ground level, while an amplifier is caused to amplify the signal on the basis of the DC level obtained by dividing by two the source voltage. Under this condition, it is difficult to separate the variation in the source voltage from the detected acceleration signals, and therefore the signals are disturbed by the effects of source voltage variation as well as external noises.

In order to cope with these problems, one solution is to replace the impedance conversion circuit with a charge amplifier. It is to be pointed out, however, that such a charge amplifier is practically difficult to adapt even in a general application which is provided with positive and negative power sources and therefore difficult technically to incorporate in general.

Furthermore, in such an automobile application it has been a problem to provide a circuit which enables the charge amplifier to be activated by a single power source and be made stable against fluctuations in the source voltage.

In addition, it is necessary to float the opposite electrodes of the piezoelectric sensor from the grounding potential in order to deploy the charge amplifier most effectively. Particularly when the casing is grounded, it is a question how to fix a piezoelectric sensor to the casing in an insulated condition.

Further, when an acceleration meter employing a piezoelectric sensor and a weight is used in an automobile, it is necessary to cancel by some means the pyroelectricity, or the characteristic that the piezoelectric sensor generates a charge depending on the change of temperature, in order to pick up only acceleration signals stably regardless of a change in the temperature of the environment.

Furthermore, when the piezoelectric sensor is used as installed in an automobile, it is necessary to remove unnecessary signals from those caused by vibration due to the operation of a suspension system, on such as vibration caused by an engine, and resonant frequencies caused by attachment of the piezoelectric sensor.

SUMMARY OF THE INVENTION

It is an object of this invention to provide an acceleration sensor which is capable of being activated by a single power source.

It is another object of this invention to provide an acceleration sensor which is stable against fluctuation in a power source voltage, external noises and irrelevant external vibrations.

It is a further object of this invention to provide an acceleration sensor which is most properly used in a wide temperature range and under a severe change of temperature.

The first and second object are achieved by an acceleration sensor comprising piezoelectric element(s) attached together with a weight to an electrically conductive casing with an insulation plate therebetween and adapted to output a detection signal depending on the rate of acceleration, and a charge amplifier for amplifying the signal output from the element(s) and a grounding circuit of which is connected to the casing.

The third object is achieved by an acceleration sensor comprising a plurality of piezoelectric elements which are connected in parallel with each other, located symmetrically, attached together with a weight to an insulation plate, and adapted to output a detection signal depending on the rate of acceleration, whereby the elements are thermally balanced.

BRIEF DESCRIPTION OF THE DRAWINGS

FIG. 4 shows a circuit diagram of the embodiment shown in FIG. 3; and

DETAILED DESCRIPTION OF THE PREFERRED EMBODIMENTS

Figure 1:
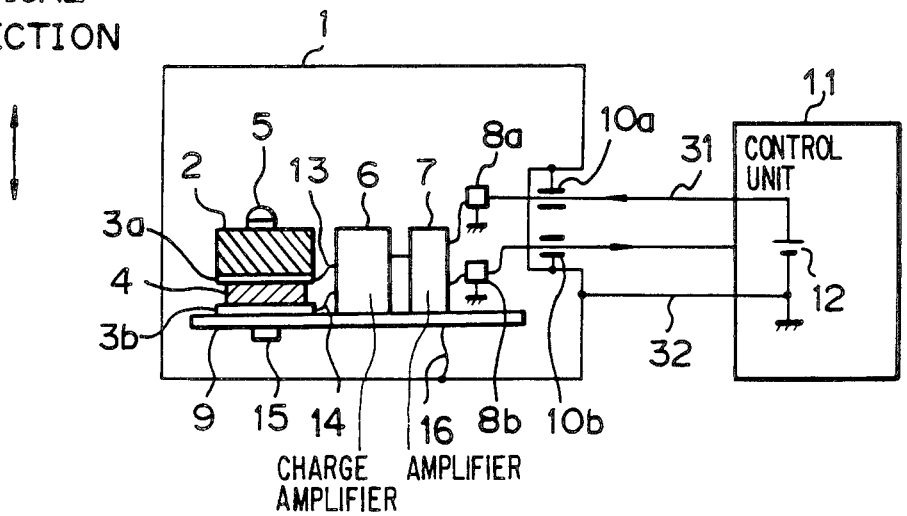
FIG. 1 illustrates a block schematic diagram showing an embodiment of this invention.

Embodiments of an acceleration sensor according to the present invention will now be explained by referring to the drawings.

FIG. 1 illustrates an embodiment of this invention. In the drawing, numeral 1 designates a conductive casing, 2 a metallic weight, 4 a piezoelectric element, 5 and 15 a fastening screw and a nut, 6 a charge amplifier and 9 an insulation plate.

The piezoelectric element 4 and the weight 2 are attached to the insulation plate 9 by the fastening screw 5 and nut 15 and the plate is fixed to a specified location (not shown) on the conductive casing 1. For the insulation plate 9, a printed circuit board comprising an epoxy resin or a ceramic board is used. This plate 9 enables the element 4 and weight 2 to be fixedly mounted to the casing in a non-conductive condition.

At the front and rear side surfaces of the element 4, there are provided electrodes 3a and 3b.

The electrode 3b at the rear side surface of the element 4 is pressed against the upper surface of the plate 9, while the electrode 3a is interposed between the weight 2 and the element 4. These electrodes 3a and 3b are respectively connected to input terminals of the charge amplifier 6 by way of output lines 13 and 14.

The charge amplifier 6 is also attached to the plate 9, and serves to amplify a detection signal from the element 4. The amplifier 6 is used for reducing a fluctuation in a source voltage and an influence by noises, because it is floated from the conductive casing 1 the potential, which is at ground potential.

Numeral 7 designates a second amplifier attached to the insulating plate 9. This amplifier 7 is used for amplifying the output from the charge amplifier 6 and has an output terminal connected to the input terminal of an electric control unit 11 by way of a three-terminal capacitor 8b and a through type capacitor 10b.

Numeral 12 designates a stabilizing power source which is available from the stabilizing power source circuit (not shown) of the control unit 11 and serves to provide the piezoelectric acceleration sensor unit including the element 4 and amplifiers 6 and 7 with the power source from its positive pole by way of a feeder line 31, a through type capacitor 10a and a three-terminal capacitor 8a.

The negative pole of the stabilizing power source 12 is grounded and also connected to the electrically conductive casing 1 by way of a grounding line 32. The conductive casing 1 is connected to an earth portion printed on the insulation plate 9 by way of a grounding line 16.

Thus constituted, the electronic circuits on the insulating plate 9, or the charge amplifier 6 and the amplifier 7, have their ground portions connected to the grounding line 32 by way of the conductive casing 1. So, the shielding effect is provided by the casing, and thereby the affect of external noise can be reduced.

Figure 2:
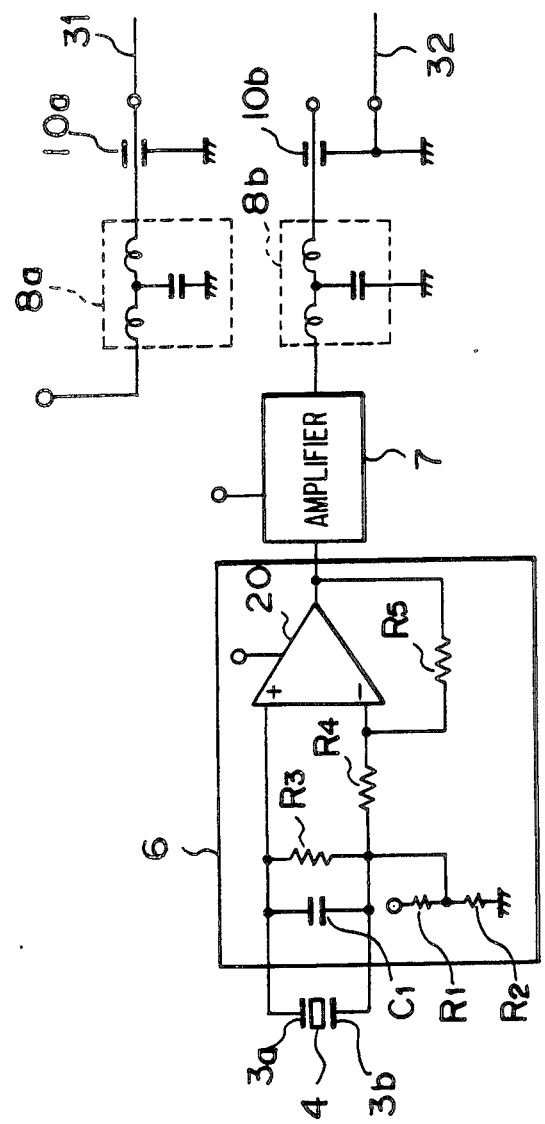
FIG. 2 is a circuit diagram of the embodiment shown in FIG. 1.

The charge amplifier 6 is so constituted as shown in FIG. 2. In FIG. 2, it is seen that the piezoelectric element 4 is floated from the grounding potential and the potential of one of the electrodes 3b is fixed to the potential provided by resistors $R_1$ and $R_2$.

In the amplifier 6, (+) input and (−) input terminals of an operational amplifier 20 having an FET input stage are connected to each other via a resistor $R_3$. Accordingly, even if the level of the power source fluctuates, their potentials of both the (+) and (−) input terminals move in unison and thereby the affect of any fluctuation in the power source on the charge amplifier 6 may be mitigated.

A capacitor $C_1$ is connected in parallel to the resistor $R_3$ and the electrode 3a of the piezoelectric element 4 is connected to the (+) input terminals of the operational amplifier 20 while the electrode 3b is connected to the (−) input terminal of the amplifier 20 via the resistor $R_4$. The capacitor $C_1$ is inserted in order to reduce the minimum detection frequency of the acceleration to be detected. For example, when the minimum detection frequency is set to 0.2 Hz, $C_1=0.047$ $\mu$F and $R_3=15$ M$\Omega$ may be set.

By using the parallel circuit of the capacitor $C_1$ and resistor $R_3$, which acts as a low pass filter unnecessary drifting voltage due to temperature change may be prevented, even if a special low pass filter is not inserted.

It is further possible to set the time constant at a low frequency range optionally and most properly by making the value of the resistor $R_3$ smaller than the input impedance of the operational amplifier 20. The input impedance of the amplifier 20 having the FET input stage is more than $10^9$ $\Omega$ and can therefore meet the above requirement.

The resistor $R_5$ is connected between the output terminal of the operational amplifier 20 and the (−) input terminal thereof. The output of the operational amplifier 20 is connected to the control unit 11 by way of the amplifier 7, the three-terminal capacitor 8b, and the through type capacitor 10b.

The grounding electrode of the capacitor 10b is connected to the negative pole of the power source 12 of the control unit 11 by way of the grounding line 32.

The power source terminal of the amplifier 7 is connected to the positive pole of the power source 12 by way of the three-terminal capacitor 8a, the through type capacitor 10a and a feeder line 31.

Operation of the acceleration sensor shown in FIGS. 1 and 2 will now be explained.

When the pressure load of the weight 2 is imposed on the piezoelectric element 4 due to acceleration, the change of the charge on the element 4 is generated depending on the rate of the acceleration and applied to the charge amplifier 6.

The charge generated by the element 4 is converted to a voltage signal by the capacitor $C_1$ and applied between the (−) and (+) input terminals of the amplifier 20. The input voltage is amplified by $(1+R_5/R_4)$ times by the operational amplifier 20 and the resistors $R_4$ and $R_5$ and further amplified by the amplifier 7, and thereafter input to the control unit 11 via the three-terminal capacitor 8b and the through type capacitor 10b.

The charge amplifier 6 is designed so as to convert the change of the charge caused by the piezoelectric element 4 to voltage and precisely amplify the converted voltage by floating the potential at the piezoelectric element 4 despite fluctuation in the source voltage. As a consequence, the charge amplifier 6 is less affected by fluctuations in the source voltage and does not particularly require a stabilizing power source exclusively for the acceleration sensor unit.

Therefore, even if the stabilizing power source 12 of the control unit 11 is used for the sensor unit and the power is supplied from the feeder line 31, the amplifier 6 may be operated in a stabilized condition.

Figure 3:
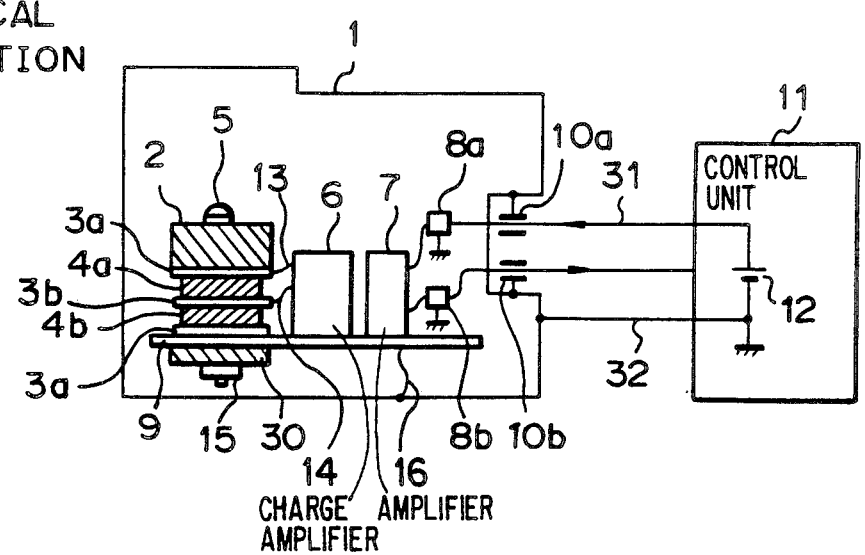
FIG. 3 illustrates a block schematic diagram showing another embodiment of this invention.

FIGS. 3 and 4 show another embodiment of this invention wherein two piezoelectric elements 4a and 4b are connected in parallel to each other instead of the single piezoelectric element 4 shown in FIGS. 1 and 2, and a metallic rigid member 30 and a capacitor $C_2$ are added to the first embodiment shown in FIGS. 1 and 2.

In this second embodiment, electrodes 3a and 3b are provided on the upper surface of the element 4a and the lower surface of the element 4b, while an electrode 3b is provided between the lower surface of the element 4a and the upper surface of the element 4b. The capacitor $C_2$ is connected between the output and input terminals of the operational amplifier 20. The metallic rigid member 30 is fixed to the insulation plate 9 together with the elements 4a and 4b and weight 2 by the metallic fixing screw 5 and nut 15.

In this way, since the metallic weight 2 and metallic rigid member 30 are fixed and thermally connected by means of the metallic fixing means, or the fixing screw 5 and nut 15, they are thermally balanced.

The electrodes 3a and 3b attached to the elements 4a and 4b are connected to the input terminals of the charge amplifier 6 by way of the feed lines 13 and 14 respectively. The two symmetric external electrodes 3a and 3b of the elements 4a and 4b are coupled by a line not shown.

The values of the capacitor $C_2$ and the resistor $R_5$, which act as a high pass filter, are set so that the time constant thereof corresponds to, for example, 5 Hz.

In the second embodiment, since there is an air layer inside the casing 1 and the elements 4a and 4b are fixed at the insulation plate 9 so as to be thermally insulated from the casing, any influence on the elements 4a and 4b from the change in the temperature outside the casing 1 is mitigated. This feature is the same as that in the first embodiment. Further, in the second embodiment, since the elements 4a and 4b retain heat due to the metallic weight 2, rigid member 30 and fastening screw 5 and nut 15, the temperature of the elements may be balanced and the gradient of the temperature change thereof may be more gentle. Furthermore, since the elements 4a and 4b are located in symmetry as well as being connected in parallel, the pyroelectricity characteristics are thus off-set.

Accordingly, by the second embodiment the affect of the pyroelectricity caused by the change in temperature may be mitigated and such pyroelectricity may be off-set by the plurality of piezoelectric elements.

By setting the time constant $C_2 \times R_5$ of the capacitor $C_2$ and the resistor $R_5$ at 5 Hz as described above, unnecessary components may be eliminated when acceleration in the vertical direction is detected.

In a prior art wherein an impedance conversion circuit is employed, setting of the time constant within a low frequency range is not easy. For this reason, it is necessary to especially provide a by-pass circuit and a low-pass filter in the later stage. However, even such a provision is not resistant to fluctuations in the source voltage. According to this second embodiment, however, only one stage comprising the charge amplifier 6 is employed to solve the problem as pointed out above.

More specifically, this embodiment is stable against fluctuations in the source voltage, resistant to temperature drifting and will not amplify any unnecessary noise caused by vibration. The acceleration sensor is most appropriate for an automobile.

Figure 5:
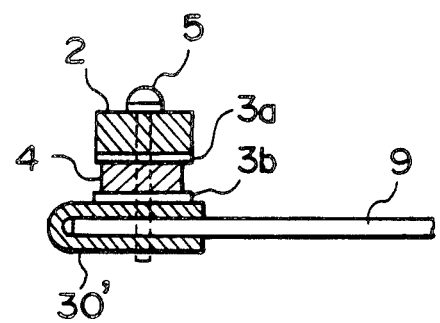
FIGS. 5 and 6 are sectional views of improved fixing portions of piezoelectric element(s) and a weight to an insulation plate according to this invention.

FIG. 5 illustrates an improvement in the method of fixing the element 4 and weight 2 shown in FIG. 1 in which detection in a vertical direction of acceleration may be stable while unnecessary detection sensitivity in a lateral direction may be reduced.

According to the embodiment shown in FIG. 1, the acceleration sensor is only intended to detect acceleration in a vertical direction. It is to be noted, however, that the piezoelectric element will be subjected to a force caused by a rolling movement due to acceleration in a lateral direction, and as a consequence, the piezoelectric element may generate an output as a result of the rolling movement.

More specifically, there is a problem as to the method of mechanically fixing the piezoelectric element 4 in a reliable manner to the casing in such a way that it is electrically insulated, according to the fixing means.

In consideration of this problem, as shown in FIG. 5, a plate 30' for reinforcing the fixing portion is used. The plate 30' is made of a rigid material such as metal, and formed into an U shape. The insulation plate 9 is inserted in the U shape plate 30' and the piezoelectric element 4 and weight 2 are placed on and fixed to the plate 30' incorporating the insulation plate 9 by the fastening screw 5 and a nut (not shown in FIG. 5), whereby any rolling movement may be reduced.

Since this plate 30' is fixed to the conductive casing 1 by way of the insulation plate 9, it can maintain its insulating function with respect to the casing 1 while it is mechanically fixed to the casing in a reliable fashion by means of screws or the like not shown, whereby acceleration detection capability in a mechanical sense may be realized as in the prior arts.

Figure 6:
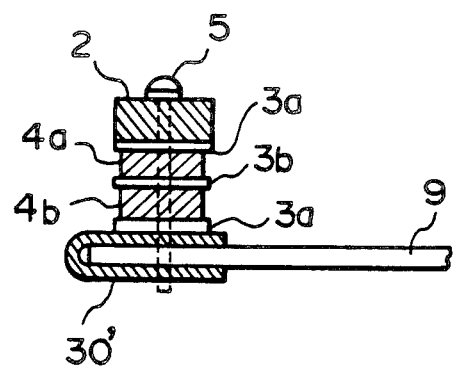

FIG. 6 shows an improved method of fixing the elements 4a and 4b and weight 2 shown in FIG. 3 in a similar manner to that shown in FIG. 5. Namely, the metallic rigid plate 30' formed into an "U" shape is used instead of the plate, or member 30 shown in FIG. 3 and the insulation plate 9 is inserted in the U shape plate 30'. The piezoelectric elements 4a and 4b and the weight 2 are fixed to the insulation plate 9, together with the plate 30', whereby any rolling movement may be reduced.

In such a case as shown in FIG. 6, thermal balancing between the elements 4a and 4b may be further optimized.

In the respective embodiments as described above, the acceleration sensor has been described as having the grounding line 32 connected between the conductive casing 1 and the earth portion of the control unit 11, or the negative pole of the battery 12, in consideration of applications requiring high accuracy. When an insulated conductive casing 1 is attached to a body of an automobile or the like, one point grounding may be attained at the electronic control unit 11, and therefor no current due to common impedance will flow through the grounding line 32. Accordingly an acceleration measurement isolated from the fluctuation in the source voltage may be made possible.

When such accuracy is not required, the conductive casing 1 may be grounded to the body of the automobile without the grounding line 32 between the casing 1 and the negative pole of the battery 12.

In the respective embodiments, although the weight 2 and piezoelectric element(s) 4 (4a, 4b) are fixed to the insulation plate which is a printed circuit board mounting the detection circuits, or the charge amplifier 6 and amplifier 7, they may be secured by separate insulation members to attain a similar effect.

Furthermore, although the detection of acceleration in the vertical direction has first been described, a similar effect may be expected in the case of the detection of acceleration in the left and right direction as well as in the forward and backward direction, if the direction of the orientation piezoelectric element(s) and weight is changed.

The invention has been described in detail with particular reference to certain preferred embodiments thereof, but it will be understood that variations and modifications can be effected within the spirit and scope of this invention. For example, in the respective embodiments, the capacitor $C_1$ for converting the change of the charge at the piezoelectric elements(s) to the corresponding voltage change may be selected such that it has a positive capacitive temperature coefficient, whereby a temperature characteristic of the detector may be compensated for. Further, the charge amplifier 6 and metallic rigid plates 30 and 30' should not be taken as being limited to those described above, and other constitutions may be employed.

What is claimed is:

1. An acceleration sensor comprising:
   a weight;
   piezoelectric means for generating a signal by a pressure load caused by said weight depending on the rate of acceleration;
   charge amplifier means connected to said piezoelectric means for amplifying said signal generated by said piezoelectric means;
   a conductive casing the potential of which is maintained at the earth level;
   an insulation plate for fixedly mounting said weight and said piezoelectric means, and being fixed to said conductive casing; and
   metallic rigid means for supporting said weight and said piezoelectric means, wherein
   said weight, said piezoelectric means and said rigid means are together fixed to said insulation plate by a means for fixing, wherein
   said metallic rigid means have an U-shaped portion, said insulation plate is inserted in said U-shaped portion and said weight, piezoelectric means and rigid means are fixed at the inserted portion of said insulation plate, and wherein
   a grounding circuit of said charge amplifier means is coupled to said conductive casing so that input terminals of said charge amplifier means are floating with respect to said earth level.

2. An acceleration sensor according to claim 1, wherein said piezoelectric means comprises two piezoelectric elements electrically connected in parallel and serially located between said weight and insulation plate through a part of said metallic rigid means, and said fixing means comprises a metallic screw and a nut, whereby said two piezoelectric elements are thermally balanced.

3. An acceleration sensor according to claim 1, wherein said insulation plate comprises a printed circuit board onto which said charge amplifier means is mounted.

4. An acceleration sensor according to claim 1, wherein said charge amplifier means comprises a first capacitor for converting said charge signal from said piezoelectric means to a voltage signal and a differential amplifier the positive input terminal of which is connected to a first electrode of said first capacitor, the negative input terminal of which is connected to a second electrode of said first capacitor through a first resistor and said negative input terminal and the output terminal of which are connected through a second resistor.

5. An acceleration sensor comprising:
   a weight;
   piezoelectric means for generating a signal by a pressure load caused by said weight depending on the rate of acceleration;
   charge amplifier means connected to said piezoelectric means for amplifying said signal generated by said piezoelectric means;
   a conductive casing the potential of which is maintained at the earth level;
   an insulation plate for fixedly mounting said weight and said piezoelectric means, and being fixed to said conductive casing, said insulating plate comprising a printed circuit board onto which said charge amplifier means is mounted; and
   metallic rigid means for supporting said weight and said piezoelectric means, wherein
   said weight, said piezoelectric means and said rigid means are together fixed to said insulation plate by a means for fixing, and wherein
   a grounding circuit of said charge amplifier means is coupled to said conductive casing so that input terminals of said charge amplifier means are floating with respect to said earth level.

6. An acceleration sensor comprising:
   a weight;
   piezoelectric means for generating a signal by a pressure load caused by said weight depending on the rate of acceleration;
   charge amplifier means connected to said piezoelectric means for amplifying said signal generated by said piezoelectric means, said charge amplifier means comprising a first capacitor for converting a charge signal from said piezoelectric means to a voltage signal and a differential amplifier the positive input terminal of which is connected to a first electrode of a said first capacitor, the negative input terminal of which is connected to a second electrode of said first capacitor through a first resistor and said negative input terminal and the output terminal of which are connected through a second resistor;
   a conductive casing the potential of which is maintained at the earth level;
   an insulation plate for fixedly mounting said weight and said piezoelectric means, and being fixed to said conductive casing; and
   metallic rigid means for supporting said weight and said piezoelectric means, wherein
   said weight, said piezoelectric means and said rigid means are together fixed to said insulation plate by a means for fixing, and wherein
   a grounding circuit of said charge amplifier means is coupled to said conductive casing so that input terminals of said charge amplifier means are floating with respect to said earth level.

7. An acceleration sensor according to claim 6, wherein said charge amplifier means further includes a second capacitor connected between said negative input terminal and output terminal of said differential amplifier, whereby said second capacitor and said second resistor form a low-pass filter.

8. An acceleration sensor according to claim 6, wherein said charge amplifier means further includes a third resistor connected in parallel to said first capacitor, whereby said third resistor and first capacitor form a high-pass filter.

* * * * *